(12) United States Patent
Gliner et al.

(10) Patent No.: US 12,178,750 B2
(45) Date of Patent: Dec. 31, 2024

(54) REMOVAL OF CATARACT DEBRIS

(71) Applicant: JOHNSON & JOHNSON SURGICAL VISION, INC., Irvine, CA (US)

(72) Inventors: Vadim Gliner, Haifa (IL); Assaf Govari, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 891 days.

(21) Appl. No.: 17/101,992

(22) Filed: Nov. 23, 2020

(65) Prior Publication Data

US 2022/0160543 A1 May 26, 2022

(51) Int. Cl.
*A61F 9/007* (2006.01)
*A61B 17/32* (2006.01)

(52) U.S. Cl.
CPC .. *A61F 9/00745* (2013.01); *A61B 17/320068* (2013.01); *A61B 2217/005* (2013.01)

(58) Field of Classification Search
CPC ............ A61F 9/00745; A61F 9/00736; A61B 17/320068; A61B 2017/32007
See application file for complete search history.

(56) References Cited

U.S. PATENT DOCUMENTS

| | | | |
|---|---|---|---|
| 2,434,480 A | 1/1948 | Anderson | |
| 3,941,122 A | 3/1976 | Jones | |
| 3,964,487 A | 6/1976 | Judson | |
| 3,990,452 A | 11/1976 | Murry et al. | |
| 4,126,137 A | 11/1978 | Archibald | |
| 4,184,510 A | 1/1980 | Murry et al. | |
| 4,808,948 A | 2/1989 | Patel et al. | |
| 4,827,911 A | 5/1989 | Broadwin et al. | |
| 4,849,872 A | 7/1989 | Gassler | |

(Continued)

FOREIGN PATENT DOCUMENTS

| CN | 109029690 A | 12/2018 |
|---|---|---|
| CN | 111557784 B | 11/2020 |

(Continued)

OTHER PUBLICATIONS

Machine translation of JP 2765803 B2 (Year: 1998).*

(Continued)

*Primary Examiner* — Laura A Bouchelle

(57) ABSTRACT

In one embodiment, a phacoemulsification apparatus includes actuators configured to vibrate responsively to respective driving signals, a needle including an aspiration channel, and configured to be vibrated by the actuators so as to emulsify a lens of an eye, a generator configured to generate at least one of the driving signals responsively to a vibration pattern selected for the needle, the needle being configured to vibrate in accordance with the selected vibration pattern, and a sensor configured to sense a level of vacuum in the aspiration channel, wherein the generator is configured to alter at least one of the driving signals to transition vibration of the needle from a first vibration pattern selected from the group consisting of a longitudinal vibration pattern and a first helical vibration pattern, to a second vibration pattern of a second helical vibration pattern, responsively to a decrease in the sensed level of vacuum.

17 Claims, 5 Drawing Sheets

(56) References Cited

U.S. PATENT DOCUMENTS

| | | | |
|---|---|---|---|
| 4,861,332 A | 8/1989 | Parisi | |
| 4,954,960 A | 9/1990 | Lo et al. | |
| 4,970,656 A | 11/1990 | Lo et al. | |
| 4,983,901 A | 1/1991 | Lehmer | |
| 5,001,649 A | 3/1991 | Lo et al. | |
| 5,026,387 A | 6/1991 | Thomas | |
| 5,062,827 A | 11/1991 | Wiksell | |
| 5,160,317 A | 11/1992 | Costin | |
| 5,162,044 A | 11/1992 | Gahn et al. | |
| 5,209,221 A | 5/1993 | Riedlinger | |
| 5,279,547 A | 1/1994 | Costin | |
| 5,318,563 A | 6/1994 | Malis et al. | |
| 5,331,951 A | 7/1994 | Kepley | |
| 5,370,602 A | 12/1994 | Kepley | |
| 5,388,569 A | 2/1995 | Kepley | |
| 5,406,503 A | 4/1995 | Williams, Jr. et al. | |
| 5,417,246 A | 5/1995 | Perkins et al. | |
| 5,431,664 A | 7/1995 | Ureche et al. | |
| 5,453,087 A | 9/1995 | Malinowski | |
| 5,520,633 A | 5/1996 | Costin | |
| 5,547,459 A | 8/1996 | Kaufman et al. | |
| 5,582,578 A | 12/1996 | Zhong et al. | |
| 5,591,127 A | 1/1997 | Barwick, Jr. et al. | |
| 5,700,240 A | 12/1997 | Barwick, Jr. et al. | |
| 5,733,256 A | 3/1998 | Costin | |
| 5,800,365 A | 9/1998 | Zhong et al. | |
| 5,808,396 A | 9/1998 | Boukhny | |
| 5,843,109 A | 12/1998 | Mehta et al. | |
| 5,852,794 A | 12/1998 | Staggs | |
| 5,979,494 A | 11/1999 | Perkins et al. | |
| 5,997,528 A | 12/1999 | Bisch et al. | |
| 6,010,496 A | 1/2000 | Appelbaum et al. | |
| 6,161,545 A | 12/2000 | Chow | |
| 6,203,516 B1 | 3/2001 | Kepley | |
| 6,394,974 B1 | 5/2002 | Kadziauskas et al. | |
| 6,402,769 B1 | 6/2002 | Boukhny | |
| 6,740,058 B2 | 5/2004 | Lal et al. | |
| 6,986,753 B2 | 1/2006 | Bui | |
| 6,997,935 B2 | 2/2006 | Anderson et al. | |
| 7,554,343 B2 | 6/2009 | Bromfield | |
| 7,713,202 B2 | 5/2010 | Boukhny et al. | |
| 7,758,538 B2 | 7/2010 | Boukhny et al. | |
| 7,811,255 B2 | 10/2010 | Boukhny et al. | |
| 8,195,286 B2 | 6/2012 | Kadziauskas et al. | |
| 8,303,613 B2 | 11/2012 | Crandall et al. | |
| 8,414,605 B2 * | 4/2013 | Gordon | A61F 9/00745 606/169 |
| 8,439,938 B2 | 5/2013 | Moore, Jr. | |
| 9,018,887 B2 | 4/2015 | Paschke | |
| 9,050,627 B2 | 6/2015 | Jacobson | |
| 9,393,152 B2 | 7/2016 | Wong et al. | |
| 9,433,723 B2 | 9/2016 | Steen et al. | |
| 10,052,227 B2 | 8/2018 | Saimovici | |
| 10,182,940 B2 | 1/2019 | Chandrakant et al. | |
| 10,363,166 B2 | 7/2019 | Raney | |
| 10,478,336 B2 * | 11/2019 | Steen | A61F 9/00745 |
| 10,478,533 B2 | 11/2019 | Borgmeier et al. | |
| 10,596,032 B2 | 3/2020 | Raney | |
| 10,596,033 B2 | 3/2020 | Urich et al. | |
| 10,857,030 B2 | 12/2020 | Raney | |
| 11,266,384 B2 | 3/2022 | Christopher et al. | |
| 2001/0003155 A1 | 6/2001 | Rockley et al. | |
| 2002/0193817 A1 | 12/2002 | Lal et al. | |
| 2004/0092921 A1 | 5/2004 | Kadziauskas et al. | |
| 2006/0079788 A1 | 4/2006 | Anderson et al. | |
| 2006/0195077 A1 | 8/2006 | Kadziauskas et al. | |
| 2009/0005712 A1 | 1/2009 | Raney | |
| 2009/0118751 A1 | 5/2009 | Wiener et al. | |
| 2011/0196404 A1 | 8/2011 | Dietz et al. | |
| 2012/0022434 A1 | 1/2012 | Lue et al. | |
| 2012/0065578 A1 | 3/2012 | Zhou | |
| 2012/0072197 A1 | 3/2012 | Ovchinnikov | |
| 2012/0143233 A1 | 6/2012 | Sinelnikov | |
| 2012/0150075 A1 | 6/2012 | Ludwin et al. | |
| 2012/0232466 A1 * | 9/2012 | Kuebler | A61M 3/0216 604/35 |
| 2013/0012868 A1 | 1/2013 | Gordon et al. | |
| 2013/0131692 A1 | 5/2013 | Kadziauskas et al. | |
| 2013/0314077 A1 | 11/2013 | Okada et al. | |
| 2014/0024969 A1 | 1/2014 | Govari et al. | |
| 2014/0163455 A1 | 6/2014 | Wilson et al. | |
| 2014/0257172 A1 | 9/2014 | Yalamanchili | |
| 2015/0133950 A1 | 5/2015 | Shelton et al. | |
| 2016/0346519 A1 | 12/2016 | Bagwell et al. | |
| 2017/0312129 A1 | 11/2017 | Kadziauskas et al. | |
| 2018/0207330 A1 | 7/2018 | Ovchinnikov et al. | |
| 2019/0099547 A1 | 4/2019 | Mehta et al. | |
| 2019/0133822 A1 | 5/2019 | Banko | |
| 2019/0321222 A1 | 10/2019 | Lieu | |
| 2020/0100851 A1 | 4/2020 | Marcuk | |
| 2021/0361481 A1 | 11/2021 | Gliner et al. | |
| 2022/0192878 A1 | 6/2022 | Algawi et al. | |
| 2022/0331159 A1 | 10/2022 | Gliner | |
| 2023/0149213 A1 | 5/2023 | Fuchs | |
| 2023/0338190 A1 | 10/2023 | Fuchs et al. | |

FOREIGN PATENT DOCUMENTS

| | | | |
|---|---|---|---|
| DE | 232755 A1 | 2/1986 | |
| DE | 3910200 A1 | 10/1990 | |
| EP | 0270819 A2 | 6/1988 | |
| EP | 0955984 B1 | 4/2004 | |
| EP | 1990032 A1 | 11/2008 | |
| EP | 3146946 A1 | 3/2017 | |
| EP | 3007660 B1 | 5/2017 | |
| IE | 920003 A1 | 7/1992 | |
| JP | H0796000 A | 4/1995 | |
| JP | 2765803 B2 * | 6/1998 | A61F 9/007 |
| WO | 0064388 A1 | 11/2000 | |
| WO | 0152782 A1 | 7/2001 | |
| WO | 2009073859 A1 | 6/2009 | |
| WO | 2016191517 A1 | 12/2016 | |

OTHER PUBLICATIONS

Leang K.K., et al., "Feedback-Linearized Inverse Feedforward for Creep, Hysteresis, and Vibration Compensation in AFM Piezoactuators," IEEE Transactions on Control Systems Technology, Sep. 1, 2007, vol. 15(5), pp. 927-935.

Baggia S., "Double-frequency Stroboscopic Method for Absolute Calibration of Vibration Transducers," Journal of Sound and Vibration, 1972, vol. 20 (1), pp. 59-69.

Castellanos-Gomez A., et al., "Calibration of Piezoelectric Positioning Actuators Using a Reference Voltage-to-displacement Transducer Based on Quartz Tuning Forks," arXiv preprint arXiv:1203.5767, 2012, 9 pages.

Chu., et al., "Ins and Outs, Get the Most Out of Today's Advanced Phaco Systems", Cataract & Refractive Surgery Today, Jan. 2016, pp. 40-45.

Edelman S., et al., "A Stroboscopic Vibration Analyzer," Journal of Research of the National Bureau of Standards—C. Engineering and Instrumentation, Oct.-Dec. 1959, vol. 63C (2), pp. 97-103.

Wikimedia Foundation., "Linear Variable Differential Transformer," Oct. 23, 2023, 3 pages. Retrieved from the Internet:[URL:https://en.wikipedia.org/wiki/ Linear_variable_differential_transformer].

Zhu et al., "Modeling of piezoelectric stack actuators considering bonding layers" Nov. 2015; Journal of Intelligent Material Systems and Structures; vol. 26; Issue 17; pp. 2418-2427. (Year: 2015).

\* cited by examiner

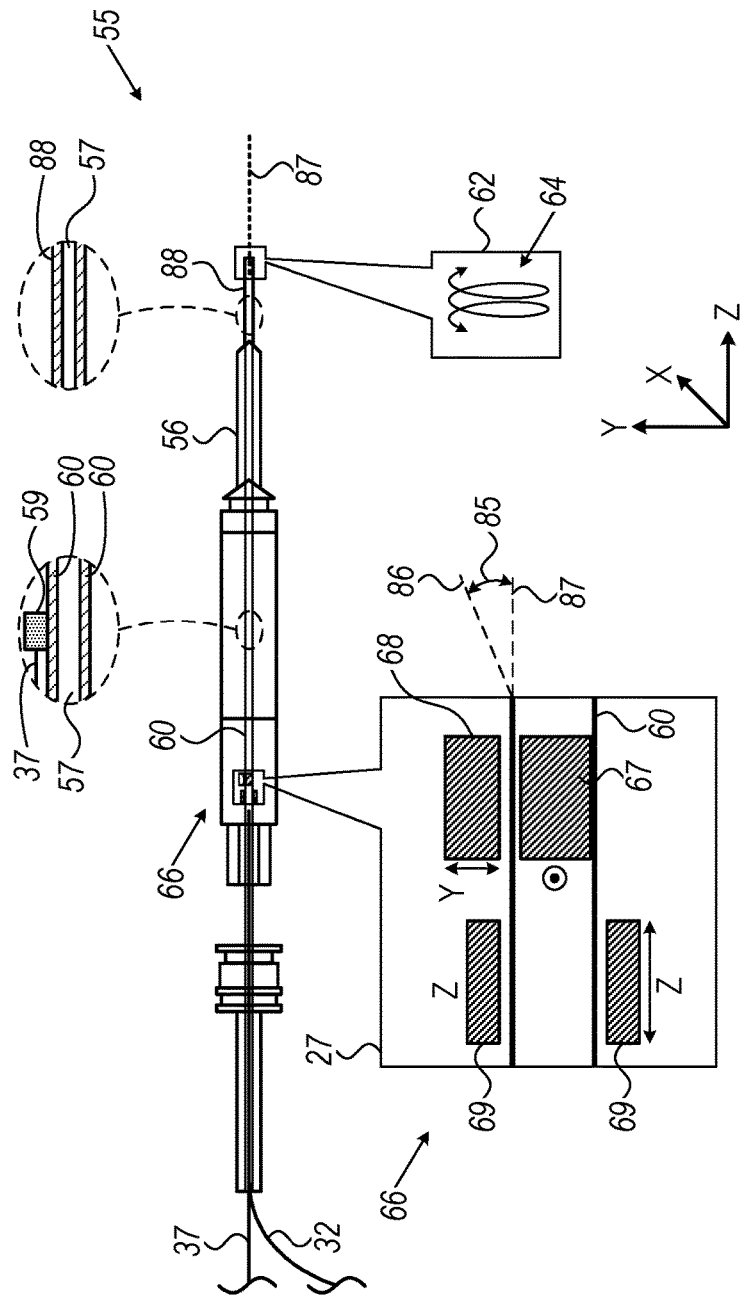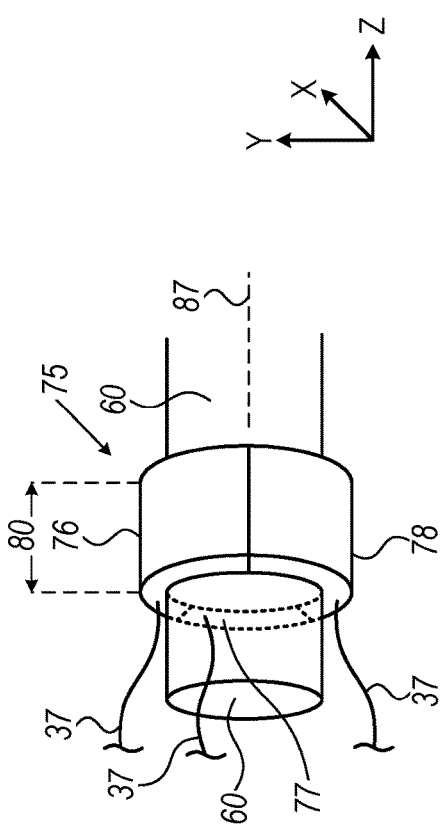
FIG. 2
FIG. 3

REMOVAL OF CATARACT DEBRIS

FIELD OF THE INVENTION

The present invention relates to medical systems, and in particular, but not exclusively to, phacoemulsification.

BACKGROUND

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this a physician may recommend phacoemulsification cataract surgery. Before the procedure, the surgeon numbs the area with anesthesia. Then a small incision is made in the sclera or clear cornea of the eye. Fluids are injected into this incision to support the surrounding structures. The anterior surface of the lens capsule is then removed to gain access to the cataract. The surgeon then uses a phacoemulsification probe, which has an ultrasonic handpiece with a titanium or steel needle. The tip of the needle vibrates at ultrasonic frequency to sculpt and emulsify the cataract while a pump aspirates lens particles and fluid from the eye through the tip. The pump is typically controlled with a microprocessor.

The pump may be a peristaltic and/or a venturi type of pump. Aspirated fluids are replaced with irrigation of a balanced salt solution to maintain the anterior chamber of the eye. After removing the cataract with phacoemulsification, the softer outer lens cortex is removed with suction. An intraocular lens (IOL) is introduced into the empty lens capsule. Small struts called haptics hold the IOL in place. Once correctly implanted the IOL restores the patient's vision.

SUMMARY

There is provided in accordance with an embodiment of the present disclosure, a phacoemulsification apparatus, including a plurality of actuators configured to vibrate responsively to respective driving signals, a needle including an aspiration channel, and configured to be vibrated by the actuators, so as to emulsify a lens of an eye, a generator configured to generate at least one of the driving signals responsively to a vibration pattern selected for the needle, the needle being configured to vibrate in accordance with the selected vibration pattern, and a pressure sensor configured to sense a level of vacuum in the aspiration channel, wherein the generator is configured to alter at least one of the driving signals to transition vibration of the needle from a first vibration pattern, which is selected from a group consisting of a longitudinal vibration pattern and a first helical vibration pattern, to a second vibration pattern including a second helical vibration pattern different from the first helical vibration pattern, responsively to a decrease in the sensed level of vacuum.

Further in accordance with an embodiment of the present disclosure the generator is configured to alter at least one of the driving signals to transition vibration of the needle from the first helical vibration pattern to the second helical vibration pattern responsively to the decrease in the sensed level of vacuum.

Still further in accordance with an embodiment of the present disclosure the first helical vibration pattern includes a first pitch and the second helical vibration pattern includes a second pitch, the first pitch being greater than the second pitch.

Additionally, in accordance with an embodiment of the present disclosure the first helical vibration pattern has a first maximum width and the second helical vibration pattern has a second maximum width, the second maximum width being greater than the first maximum width.

Moreover, in accordance with an embodiment of the present disclosure the first helical vibration pattern includes a first pitch and the second helical vibration pattern includes a second pitch, the first pitch being greater than the second pitch.

Further in accordance with an embodiment of the present disclosure the first helical pattern and the second helical pattern are circular helical patterns, the first helical pattern having a diameter equal to the first maximum width, the second helical pattern having a diameter equal to the second maximum width.

Still further in accordance with an embodiment of the present disclosure the first helical pattern and the second helical pattern are elliptical helical patterns, the first helical pattern having a long axis equal to the first maximum width, the second helical pattern having a long axis equal to the second maximum width.

Additionally, in accordance with an embodiment of the present disclosure the generator is configured to alter at least one of the driving signals to transition vibration of the needle from the longitudinal vibration pattern to the second helical vibration pattern responsively to the decrease in the sensed level of vacuum.

Moreover, in accordance with an embodiment of the present disclosure the longitudinal vibration pattern has a first longitudinal stroke length, the second helical vibration pattern having a second longitudinal stroke length, which is less than the first longitudinal stroke length.

Further in accordance with an embodiment of the present disclosure the generator is configured to alter at least one of the driving signals to further transition vibration of the needle from the second helical vibration pattern to a two-dimensional elliptical pattern.

Still further in accordance with an embodiment of the present disclosure the generator is configured to alter at least one of the driving signals to further transition vibration of the needle back to the first vibration pattern responsively to expiration of a delay.

There is also provided in accordance with another embodiment of the present disclosure, a phacoemulsification method, including generating driving signals responsively to a vibration pattern selected for vibrating a needle, vibrating actuators responsively to the driving signals, vibrating the needle in accordance with the selected vibration pattern responsively to vibrating of the actuators so as to emulsify a lens of an eye, sensing a level of vacuum in an aspiration channel of the needle, and altering at least one of the driving signals to transition vibration of the needle from a first vibration pattern, which is selected from a group consisting of a longitudinal vibration pattern and a first helical vibration pattern, to a second vibration pattern including a second helical vibration pattern different from the first helical vibration pattern, responsively to a decrease in the sensed level of vacuum.

Additionally, in accordance with an embodiment of the present disclosure the altering includes altering at least one of the driving signals to transition vibration of the needle from the first helical vibration pattern to the second helical vibration pattern responsively to the decrease in the sensed level of vacuum.

Moreover, in accordance with an embodiment of the present disclosure the first helical vibration pattern includes a first pitch and the second helical vibration pattern includes a second pitch, the first pitch being greater than the second pitch.

Further in accordance with an embodiment of the present disclosure the first helical vibration pattern has a first maximum width and the second helical vibration pattern has a second maximum width, the second maximum width being greater than the first maximum width.

Still further in accordance with an embodiment of the present disclosure the first helical vibration pattern includes a first pitch and the second helical vibration pattern includes a second pitch, the first pitch being greater than the second pitch.

Additionally, in accordance with an embodiment of the present disclosure the first helical pattern and the second helical pattern are circular helical patterns, the first helical pattern having a diameter equal to the first maximum width, the second helical pattern having a diameter equal to the second maximum width.

Moreover, in accordance with an embodiment of the present disclosure the first helical pattern and the second helical pattern are elliptical helical patterns, the first helical pattern having a long axis equal to the first maximum width, the second helical pattern having a long axis equal to the second maximum width.

Further in accordance with an embodiment of the present disclosure the altering includes altering at least one of the driving signals to transition vibration of the needle from the longitudinal vibration pattern to the second helical vibration pattern responsively to the decrease in the sensed level of vacuum.

Still further in accordance with an embodiment of the present disclosure the longitudinal vibration pattern has a first longitudinal stroke length, the second helical vibration pattern having a second longitudinal stroke length, which is less than the first longitudinal stroke length.

Additionally, in accordance with an embodiment of the present disclosure, the method includes altering at least one of the driving signals to further transition vibration of the needle from the second helical vibration pattern to a two-dimensional elliptical pattern responsively to a further decrease in the sensed level of vacuum.

Moreover, in accordance with an embodiment of the present disclosure, the method includes altering at least one of the driving signals to further transition vibration of the needle back to the first vibration pattern responsively to expiration of a delay.

BRIEF DESCRIPTION OF THE DRAWINGS

The present invention will be understood from the following detailed description, taken in conjunction with the drawings in which:

FIG. 2 is a schematic pictorial illustration of a phacoemulsification handpiece for use in the system of FIG. 1;

FIG. 3 is a schematic pictorial illustration of an actuator assembly of an alternative phacoemulsification handpiece for use in the system of FIG. 1;

DESCRIPTION OF EXAMPLE EMBODIMENTS

Overview

Figure 1:
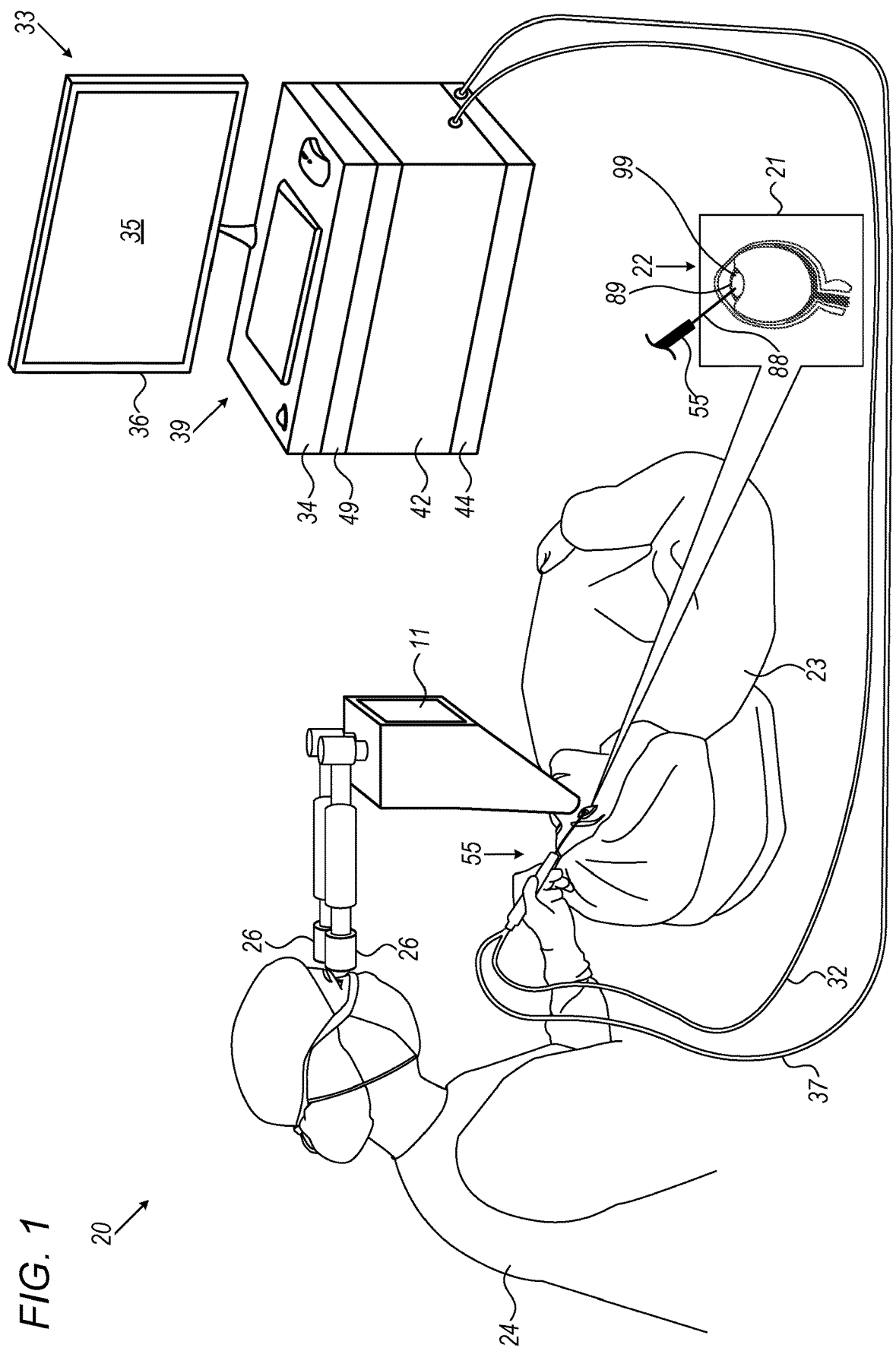
FIG. 1 is a schematic pictorial illustration of an ophthalmic surgical system constructed and operative in accordance with an embodiment of the present invention.

As previously mentioned, a surgeon uses a phacoemulsification probe, which has an ultrasonic handpiece with a titanium or steel needle. The tip of the needle vibrates at ultrasonic frequency to sculpt and emulsify the cataract while a pump aspirates lens particles and fluid from the eye through the tip. The needle is vibrated by a piezoelectric crystal, so that the needle acts as an "impact drill", drilling into the lens using longitudinal vibrations, for example. The drilling may cause lens particles (that are removed by the needle action) to be ejected and dispersed into fluid surrounding the lens, forming what is termed "cataract milk" or "phaco smoke". The milk may occlude light from reaching the retina and it is very important that the milk is removed as part of the cataract procedure.

One solution is to toggle between longitudinal and transverse vibration modes of a piezoelectric crystal. During the longitudinal vibration phases the lens is broken into particles, some of which are aspirated during the longitudinal phases, while some of the particles are dispersed into the surrounding eye fluid. During the transverse vibration phases some of the dispersed particles are aspirated. This proposed solution has a number of problems. First, it is important to limit the overall vibrations as the vibrations lead to heating of the needle and could damage structures of the eye. Second, transverse vibration may not remove all the dispersed particles as the particles are dispersed in all directions whereas the transverse vibrations have a limited directional freedom of movement. Third, the rate of toggling between the vibration modes is limited, because of the very high self-capacitance of the piezoelectric crystal, and this limits how well the overall vibrational energy can be minimized while effectively removing the dispersed particles.

Embodiments of the present invention solve the above problems by providing a phacoemulsification apparatus with multiple actuators which vibrate a needle to emulsify a lens of an eye responsively to generated driving signals. The actuators allow the apparatus to toggle smoothly and quickly between different modes of vibrations, e.g., longitudinal vibrations which are efficient at emulsifying the lens, elliptical (e.g., circular) vibrations in which the tip of the needle repeatedly moves in complete ellipses (e.g., circles), and helical vibrations in which the needle moves to repeatedly describe a helical shape. Elliptical and helical vibrations are effective at sweeping around the eye fluid to remove the dispersed particles.

In some embodiments, in order to minimize heating the eye, a balance between emulsifying the lens and removing dispersed particles is maintained responsively to a sensed vacuum in an aspiration channel of the needle. The needle vibrates with a longitudinal vibration pattern to emulsify the lens when the sensed vacuum is sufficiently high (above a given limit). The sufficiently high vacuum indicates that there is good contact between the tip of the needle and the lens so that the longitudinal vibrations are acting to sufficiently emulsify the lens. However, when the sensed vacuum is lower than a given limit, indicating the that the longitudinal vibrations are less successful at emulsifying the lens, the needle transitions to vibrating with a helical vibration pattern having more circular motion to focus on removing dispersed particles. The helical vibration pattern may have a shorter longitudinal stroke length that when the needle was vibrating with the longitudinal vibration pattern. In some embodiments, the helical vibration pattern may have the same longitudinal stroke length as when the needle was vibrating with the longitudinal vibration pattern. In some embodiments, the longitudinal vibration component of the helical vibration pattern is reduced until the needle is transitioned to vibrating with a two-dimensional elliptical (e.g., circular) vibration pattern.

In some embodiments, the needle vibrates with a first helical vibration pattern to emulsify the lens when the sensed vacuum is sufficiently high. However, when the sensed vacuum is lower than a given limit, the needle transitions to vibrating with a second helical vibration pattern having more circular motion and/or less longitudinal motion to focus more on removing dispersed particles. For example, the second helical pattern has a smaller pitch and/or a larger maximum width than the first helical pattern. The maximum width of the helical pattern may be defined as the diameter of the helical pattern when the helical pattern is circular, or the long axis of an ellipse when the helical pattern is elliptical.

The vibration of the needle is transitioned back to the initial vibration pattern (e.g., longitudinal vibration pattern or the first helical vibration pattern) responsively to expiration of a delay or a restoration of vacuum level. In some embodiments, the amount of elliptical/circular motion versus the amount of longitudinal motion is set proportionally to the sensed vacuum so that the amount of longitudinal motion is relatively higher when the sensed vacuum is higher and the amount of elliptical/circular motion is relatively higher when the sensed vacuum is lower.

System Description

FIG. 1 is a schematic pictorial illustration of an ophthalmic surgical system 20, in accordance with an embodiment of the present invention. System 20 is configured to carry out various types of ophthalmic procedures, such as but not limited to a cataract surgery.

In some embodiments, system 20 comprises a medical instrument, in the present example a phacoemulsification handpiece, also referred to herein as a tool 55, used by a surgeon 24 to carry out the cataract surgery. In other embodiments, system 20 may comprise other surgical tools, such as but not limited to an irrigation and aspiration (I/A) handpiece, a diathermy handpiece, a vitrectomy handpiece, and similar instruments.

Reference is now made to an inset 21 showing a sectional view of the surgical procedure carried out in an eye 22 of a patient 23. In some embodiments, surgeon 24 applies tool 55 for treating eye 22, and in the present example, surgeon 24 inserts a needle 88 of tool 55 into eye 22. In the example of inset 21, during a cataract surgical procedure, surgeon 24 inserts needle 88 into a capsular bag 89 so as to emulsify a lens 99 of eye 22.

Reference is now made back to the general view of FIG. 1. In some embodiments, system 20 comprises a console 33, which comprises a processor 34, a memory 49, a generator 44 and a cartridge 42. In some embodiments, cartridge 42 comprises pumping sub-systems (not shown) configured to apply, via multiple tubes 32, irrigation fluids (not shown) into eye 22 and to draw eye fluids away from eye 22 into cartridge 42. In the context of the present invention, the term "eye fluid" refers to any mixture of natural eye fluid, irrigation fluid and lens material. Note that tubes 32 may comprise an irrigation tube for supplying the irrigation fluid into eye 22, and a separate aspiration tube for drawing the eye fluids away from eye 22.

In some embodiments, generator 44 is electrically connected to tool 55, via a plurality of wires (shown in FIG. 3 below) referred to herein as an electrical cable 37. Generator 44 is configured to generate one or more voltage periodic (e.g., sinusoidal) signals, also referred to herein as periodic signals, having one or more frequencies, respectively. Generator 44 is further configured to generate a plurality of driving signals, so as to vibrate needle 88 of tool 55 in accordance with a predefined pattern, so as to emulsify lens 99 of eye 22. Embodiments related to the periodic signals and driving signals are described in detail in FIGS. 2-5 below.

In some embodiments, processor 34 typically comprises a general-purpose computer, with suitable front end and interface circuits for controlling generator 44, cartridge 42 and other components of system 20.

In practice, some or all of the functions of the process 34 may be combined in a single physical component or, alternatively, implemented using multiple physical components. These physical components may comprise hard-wired or programmable devices, or a combination of the two. In some embodiments, at least some of the functions of the processor 34 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

In some embodiments, system 20 comprises an ophthalmic surgical microscope 11, such as ZEISS OPMI LUMERA series or ZEISS ARTEVO series supplied by Carl Zeiss Meditec AG (Oberkochen, Germany), or any other suitable type of ophthalmic surgical microscope provided by other suppliers. Ophthalmic surgical microscope 11 is configured to produce stereoscopic optical images and two-dimensional (2D) optical images of eye 22. During the cataract surgery, surgeon 24 typically looks though eyepieces 26 of ophthalmic surgical microscope 11 for viewing eye 22.

In some embodiments, console 33 comprises a display 36 and other input device 39, which may be used by surgeon 24 for controlling tool 55 and other components of system 20. Moreover, processor 34 is configured to display on display 36, an image 35 received from any suitable medical imaging system for assisting surgeon to carry out the cataract surgery.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of ophthalmic and other minimally invasive and surgical systems.

Vibrating a Needle of a Phacoemulsification Handpiece in Accordance with a Predefined Pattern to Carry Out a Cataract Surgery FIG. 2 is a schematic pictorial illustration of tool 55, in accordance with an embodiment of the present invention. In some embodiments, tool 55 comprises needle 88 and a coaxial irrigation sleeve 56 that at least partially surrounds needle 88 and creates a fluid pathway between the external wall of the needle and the internal wall of the irrigation sleeve. Note that needle 88 is hollow and includes an aspiration channel 57 through which fluids (e.g., natural eye fluid, irrigation fluid and lens material) are aspirated from the patient's eye during the cataract surgery. The needle has a direction of elongation parallel to a longitudinal axis 87. The aspiration channel 57 connects with one of the tubes 32 for aspirating the fluids into the cartridge 42 (FIG. 1).

The tool 55 includes a pressure sensor 59 configured to sense a level of vacuum in the aspiration channel 57. The pressure sensor 59 may be connected via a wire in the electrical cable 37 to the console 33. The pressure sensor 59 provides a signal indicative of the pressure in the aspiration channel 57. The pressure in the aspiration channel 57 is indicative of a level of vacuum in the aspiration channel 57. The level of vacuum in the aspiration channel 57 provides an indication of the quality of contact between a tip of the needle 88 and the lens 99, as described in more detail below with reference to FIGS. 6 and 7.

In other embodiments, needle 88 or another suitable element of tool 55 may be able to transfer irrigation fluid from the irrigation tube (described in FIG. 1 above) to the patient's eye.

In some embodiments, tool 55 comprises an actuator assembly 66 comprising multiple actuators configured to vibrate responsively to respective driving signals. In the present example the actuator assembly 66 includes three actuators 67, 68 and 69 made from piezoelectric crystals and coupled with a shaft 60, for driving vibration of needle 88. The piezoelectric crystals are configured to vibrate needle 88 in a resonant vibration mode in response to receiving, via cable 37, driving signals from generator 42, so as to emulsify the lens 99 of the eye 22. The vibration of needle 88 is used for breaking the cataract of the patient's eye into small pieces, e.g., constitutes the aforementioned lens material, during the phacoemulsification procedure.

Reference is now made to an inset 27 showing actuator assembly 66. In some embodiments, actuators 67-69 are placed in contact with shaft 60. In the example of FIG. 2, actuator 69 has a toroidal shape surrounding and coupled with shaft 60. Actuator 69 is configured, in response to receiving a driving signal also referred to herein as a first driving signal, to vibrate along a Z-axis of an XYZ coordinate system.

In the context of the present invention and in the claims, the terms "first driving signal," "second driving signal" and "third driving signal" refer to similar or different driving signals, which are applied to actuators 69, 68 and 67, respectively, and are indexed using the terms "first," "second" and "third."

In some embodiments, actuator 68 is coupled with shaft 60 and is configured, in response to receiving the second driving signal, to vibrate along a Y-axis of the XYZ coordinate system. Similarly, actuator 67 is coupled with shaft 60 and configured, in response to receiving the third driving signal, to vibrate along an X-axis of the XYZ coordinate system.

In some embodiments, generator 44 is configured to selectively generate one or more of the driving signals responsively to a vibration pattern selected for the needle 88. The needle 88 is configured to vibrate in accordance with the selected vibration pattern. In the example of FIG. 2, generator 44 is configured to apply voltage signals of the aforementioned first, second and third driving signals having a frequency range between about 26 kHz (kilo hertz) and 130 kHz, with a preferred frequency of about 40 kHz, e.g. 39.4 kHz. When applying the first driving signal to actuator 69, actuator assembly 66 generates a vibration (back and forth) in a Z-axis, so that the vibration generated by actuator assembly 66 is typically parallel to longitudinal axis 87 of needle 88.

In some embodiments, when applying the first, second and third driving signals to actuators 69, 68 and 67, respectively, a vibration axis 86 may have an angle 85 relative to longitudinal axis 87, in the XYZ space, as shown in inset 27.

In some embodiments, generator 44 is further configured to apply at least two of the driving signals with a phase difference. For example, generator 44 is configured to generate a circular shape of a vibration pattern in an XY plane, by applying to actuators 68 and 67 the respective second and third driving signals, with a phase difference of 90 degrees. Moreover, when generating the circular shape of the vibration pattern, generator 44 is configured to define the diameter size of a circular vibration of needle 88 by controlling the amplitude of the second driving signal and the third driving signal applied to actuators 68 and 67, respectively.

In other embodiments, generator 44 is configured to define an elliptical shape of the needle vibration, by setting the phase difference to differ from 90 degrees. In such embodiments, generator 44 is configured to define the size of the long and short axes of the ellipse, by controlling the amplitude of the second driving signal and the third driving signal applied to actuators 68 and 67, respectively.

Reference is now made to an inset 62 showing the vibration pattern of needle 88 in response to the driving signals supplied by generator 44. In an embodiment, generator 44 is configured to generate a helical pattern 64 of needle 88 by combining the circular shape of vibration pattern in the XY plane, as described above, with a linear vibration in the Z-axis, which is produced by applying the first driving signal to actuator 69. Note that the amplitude of each driving signal is indicative of the vibration range. For example, generator 44 is configured to control the step (along Z-axis) of helical pattern 64, by controlling the voltage amplitude of the first driving signal.

Reference is now made back to inset 27, by controlling the amplitude of the second and third driving signals, without applying a phase difference between driving signals, generator 44 is configured to control angle 85 between vibration axis 86 and longitudinal axis 87 of needle 88. In some embodiments, generator 44 is configured to vibrate needle 88 symmetrically with respect to vibration axis 86, which is not parallel to longitudinal axis 87. For example, generator 44 is configured to generate an angle of 45 degrees in the XY plane, between axes 86 and 87 by applying the same voltage amplitude to actuators 67 and 68.

Note that the frequency of the driving signals is determined for obtaining resonance in the driven actuators, and is based on various parameters, such as the structure of the actuators (e.g., piezoelectric) material, the size of the actuators, and interactions between elements of the actuator assembly and other elements, such as shaft 60.

This particular configuration of tool 55 and actuator assembly 66 are simplified and shown by way of example, in order to illustrate certain problems that are addressed by embodiments of the present invention and to demonstrate the application of these embodiments in enhancing the performance of such a phacoemulsification system. Embodiments of the present invention, however, are by no means limited to this specific sort of example phacoemulsification handpiece and actuator assembly, and the principles described herein may similarly be applied to other sorts of phacoemulsification handpieces and actuator assemblies used in ophthalmic surgical systems.

FIG. 3 is a schematic pictorial illustration of an actuator assembly 75 of a phacoemulsification handpiece, in accordance with another embodiment of the present invention. Actuator assembly 75 may replace, for example, actuator assembly 66 of FIG. 2 above.

In some embodiments, actuator assembly 75 comprises three actuator 76, 77 and 78, which are coupled with one another and are arranged in a toroidal shape. In the present example, actuators 76-78 are made from any suitable type of piezoelectric materials, e.g., piezoelectric materials similar to that of actuators 67-69 described in FIG. 2 above.

In some embodiments, actuator assembly 75 is coupled with and surrounds shaft 60 at any suitable position along the Z-axis of shaft 60. Actuator assembly 75 has a size 80 (e.g., between about 10 mm and 60 mm) in the Z-axis, typically, but not necessarily, similar to all actuators 76, 77 and 78.

In some embodiments, actuators 76, 77 and 78 are configured to receive from generator 44, first, second and third driving signals, respectively, using the same techniques described in FIGS. 1 and 2 above. In vibration, actuators 76, 77 and 78 are configured to deflect needle 88 from longitudinal axis 87 of needle 88 in a first direction, a second direction and a third direction, respectively. The first, second and third directions are determined by the first, second and third driving signals, respectively, as described herein.

In some embodiments, generator 44 is configured to apply a voltage signal having the same frequency (e.g., about 40 kHz) and same amplitude, to actuators 76, 77 and 78 in the first, second and third driving signals, respectively. In response to the driving signals, actuators 76-78 of actuator assembly 75 are configured to lengthen and shorten mutually and evenly along Z-axis, and thereby, to vibrate needle solely in Z-axis.

In some embodiments, generator 44 is configured to form a three-dimensional (3D) vibration pattern by applying a phase difference between at least two of the first driving signal, the second driving signal, and the third driving signal. For example, generator 44 is configured to generate the first, second and third driving signals with (i) the same frequency and amplitude, (ii) without phase difference between the first and second, and (iii) with a phase difference (e.g., of 180 degrees) between the second and third driving signals. In such embodiments, actuator assembly 75 is configured to oscillate in the XYZ space because actuators 76 and 77 elongate and actuator 78 shortens at the same time. For example, in response to a phase difference between at least two of the driving signals applied to actuators 76-78, the resonance frequency in actuators 76-78 of actuator assembly 75 may be altered from a first frequency (e.g. about 40 kHz) to a second frequency (e.g. about 27 kHz). The different resonance frequency may be caused by a difference in the intrinsic mechanical resistance of actuator assembly 75, for the movement described above, or from any other reason. Note that the resonance frequencies of about 40 kHz and 27 kHz are provided by way of example, and in other embodiments, the actuators of actuator assemblies 66 and 75 may have any other suitable resonance frequencies determined by the dimensions and material of the actuators.

In some embodiments, generator 44 is configured to derive at least one of the first, second and third driving signals from a combination of two periodic signals. In the present example, generator 44 is configured to generate a sequence of two voltage sinusoidal signals, wherein one of the signals has a first frequency, e.g., between about 26 kHz and 130 kHz, preferably a frequency of about 40 kHz, e.g. 39.4 kHz. The other signal has a second, different frequency, e.g., between about 17 kHz and 80 kHz, and preferably a frequency of about 27 kHz or any other suitable frequency within this range. Note that the frequency used in the driving signals can be identical or about the same for the first, second and third driving signals, depending on the required vibration pattern. In such embodiments, at a first time interval, generator 44 is configured to apply the same driving signal having a frequency of about 40 kHz (or any other suitable frequency selected within the range between about 26 kHz and 130 kHz described above) to all of actuators 76-78. This means that in this case no phase difference exists between the driving signals applied to the actuators. Note that when the vibration is required to be precisely parallel to axis 87, it is important to apply the same frequency and amplitude to all of actuators 76-78, without phase difference between the first, second and third driving signals. At a second, different, time interval, generator 44 is configured to apply the driving signal having a frequency of about 27 kHz, e.g. 18.8 kHz, or any other suitable frequency selected within the range between about 17 kHz and 80 kHz described above, to actuators 76-78, wherein in this case a suitable phase difference (e.g., of 180 degrees) exists between any pair of driving signals applied to actuators 76-78 (e.g., between driving signals applied to actuators 76 and 77). Generator 44 is further configured to generate at least one of the first, second and third driving signal, by repeatedly applying a sequence comprising applying the driving signal having a frequency of about 40 kHz during a first time interval followed by applying the driving signal having a frequency of about 27 kHz during a second time interval.

In some embodiments, generator 44 is configured to set different amplitudes to at least two of the first, second and third driving signals. In such embodiments, similarly to the description above, in response to the driving signals having a frequency of about 40 kHz, actuator assembly 75 vibrates along Z-axis, and in response to the driving signals having a frequency of about 27 kHz (having an appropriate phase difference), actuator assembly 75 vibrates needle 88 in a three-dimensional (3D) vibration pattern.

In some embodiments, using the techniques described above, generator 44 is configured to cause needle 88 to vibrate in accordance with any desired vibration pattern (e.g., longitudinal, traverse, elliptical, helical, or a combination thereof). The vibration pattern is achieved by applying the first, second and third driving signals to actuators 76, 77 and 78, respectively, using a suitable combination of the driving signal having a frequency of about 40 kHz and the driving signal having a frequency of about 27 kHz with selected phase differences and/or amplitude differences among the first, second and third driving signals.

In alternative embodiments, actuators 76, 77 and 78 are distributed around longitudinal axis 87 of needle 88 without being coupled with one another. In such embodiments, actuators 76, 77 and 78 are still configured to vibrate along vibration axis 86 in response to the first, second and third driving signals, respectively, as described above. Additionally, or alternatively, at least two of actuators 76, 77 and 78 may be coupled with one another using any suitable connecting element made from any suitable material and having any suitable geometry.

In other embodiments, actuators 76-78 are coupled with one another and are mutually arranged such that actuator assembly 75 has a solid cylindrical shape. In such embodiments, actuator assembly 75 is coupled with the proximal end of shaft 60, so as to vibrate needle 88 in accordance with any suitable predefined pattern using the techniques described above. In yet other embodiments, actuator assembly 75 may have any other suitable shape configured for vibrating needle 88 in accordance with any suitable pattern. In such embodiments, tool 55 may have any other suitable configuration (in addition to or instead of shaft 60) for transmitting the aforementioned vibrations to needle 88.

In yet alternative embodiments, actuator assembly 75 may comprise any suitable number of actuators, wherein at least some of them are coupled together.

Figure 4:
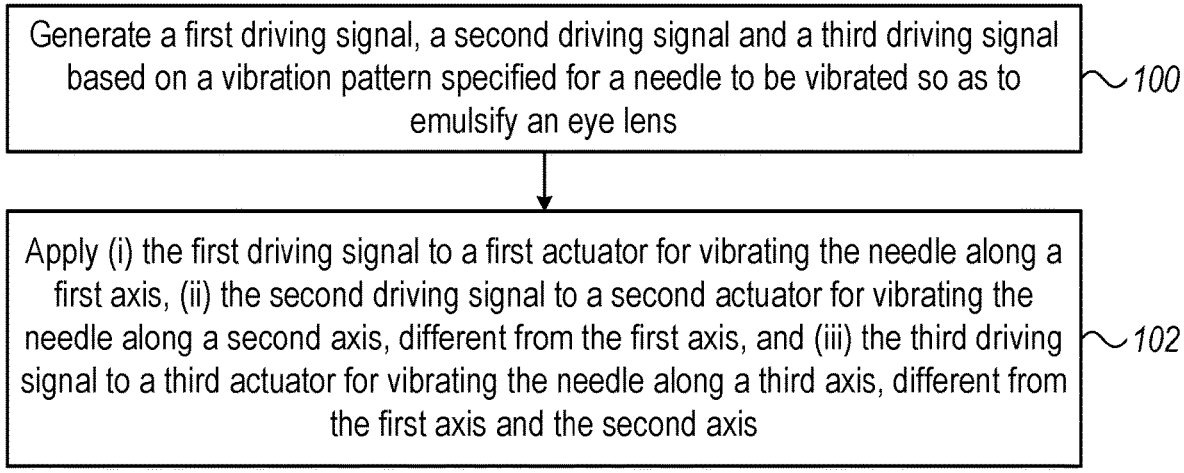
FIGS. 4 and 5 are flow charts that schematically illustrate methods for emulsifying a lens of an eye by vibrating a needle using a predefined pattern, in accordance with embodiments of the present invention.

FIG. 4 is a flow chart that schematically illustrates a method for emulsifying lens 99 of eye 22 by vibrating needle 88 using a predefined pattern, in accordance with an embodiment of the present invention.

The method begins at a driving signal generation step (block 100), with generating, e.g., using generator 44, a first driving signal, a second driving signal and a third driving signal. As described in FIG. 2 above, the first, second and third driving signals have a first frequency (e.g., between about 27 kHz and 130 kHz, with a preferred selected frequency of about 40 kHz) and are generated based on a vibration pattern specified for needle 88 to be vibrated so as to emulsify lens 99 of eye 22.

At a driving signal applying step (block 102) that concludes the method, generator 44 applies: (i) the first driving signal to actuator 69 for vibrating needle 88 along the Z-axis, (ii) the second driving signal to actuator 68 for vibrating needle 88 along the Y-axis, and (iii) the third driving signal to actuator 67 for vibrating needle 88 along the X-axis.

In some embodiments, generator 44 is configured to control a phase difference of about 90 degrees between the second driving signal and the third driving signal, so as to define a circular shape for a helical vibration pattern applied to needle 88, as described in FIG. 2 above.

Figure 5:
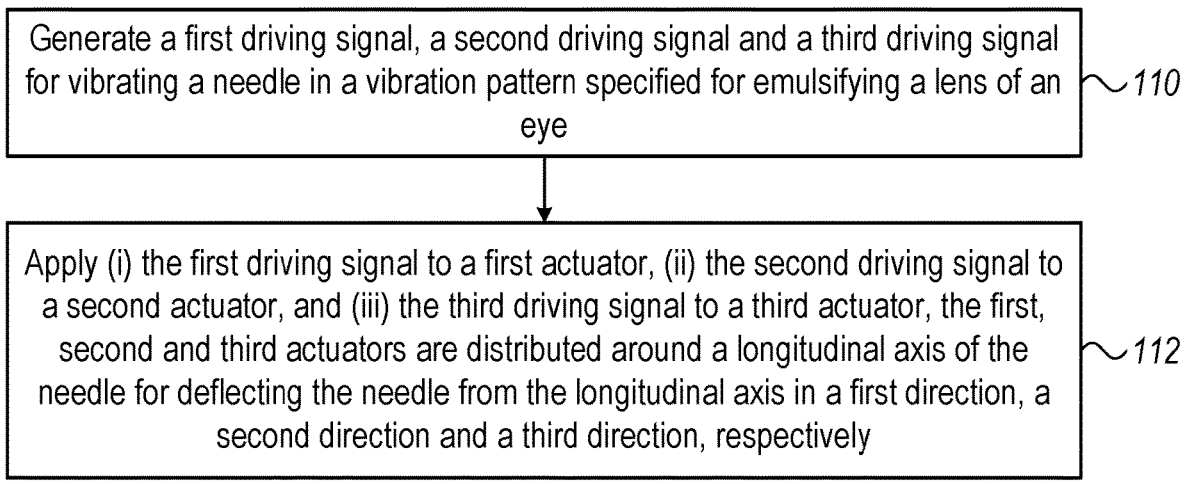

FIG. 5 is a flow chart that schematically illustrates a method for emulsifying lens 99 of eye 22 by vibrating needle 88 using a predefined pattern, in accordance with another embodiment of the present invention.

The method begins at a driving signal generation step (block 110), with generating, e.g., using generator 44, a first driving signal, a second driving signal and a third driving signal for vibrating needle 88 in a vibration pattern specified for emulsifying lens 99 of eye 22.

In some embodiments that are described in FIG. 3 above, generator 44 generates a first periodic signal having a first frequency (e.g., between about 27 kHz and 130 kHz, with a preferred selected frequency of about 40 kHz) and a second periodic signal having a second frequency (e.g., between about 17 kHz and 80 kHz, with a preferred selected frequency of about 27 kHz), and derives at least one of the first driving signal, the second driving signal and the third driving signal from the first periodic signal and the second periodic signal. Generator 44 generates at least one of the first driving signal, the second driving signal and the third driving signal, by repeatedly applying a sequence comprising applying the first periodic signal during a first time interval followed by applying the second periodic signal during a second time interval.

At a driving signal applying step (block 112) that concludes the method, generator 44 applies: (i) the first driving signal to actuator 76, (ii) the second driving signal to actuator 77, and (iii) the third driving signal to actuator 78. As shown in FIG. 3 above, actuators 76-78 are distributed around longitudinal axis 87 of needle 88 for deflecting the needle from longitudinal axis 88 in a first direction, a second direction and a third direction, respectively. In some embodiments, during the second time interval, generator 44 may apply the first driving signal with a phase difference relative to the second driving signal so as to obtain the specified vibration pattern, as described in detail in FIG. 3 above. Moreover, generator 44 may set different amplitudes to at least two of the first, second and third driving signals, so as to obtain the specified vibration pattern.

Figure 6:
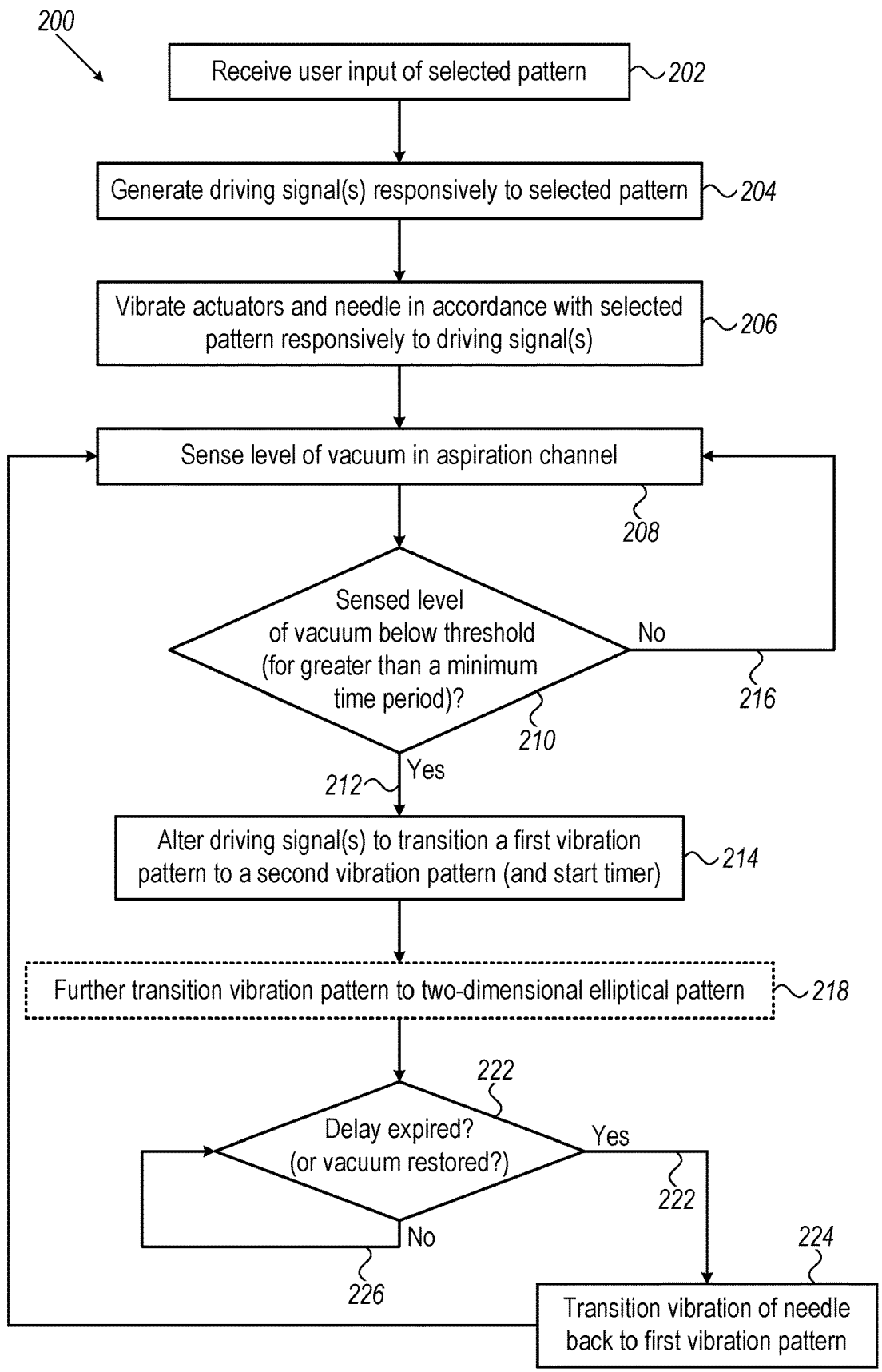
FIG. 6 is a flowchart including steps in a method of operation of the system of FIG. 1.

Reference is now made to FIG. 6, which is a flowchart 200 including steps in a method of operation of the system of FIG. 1.

The processor 34 (FIG. 1) is configured to receive a user input of a selected vibration pattern via the input device 39 (FIG. 1) (block 202). The processor 34 is configured to provide instructions to the generator 44 to generate driving signal(s) responsively to the selected vibration pattern. The generator 44 is configured to generate at least one of the driving signals responsively to the vibration pattern selected for the needle 88 (e.g., based on the instructions provided by the processor 34) (block 204).

One or more of the actuators (67-69 of FIG. 2 or 76-78 of FIG. 3) are configured to vibrate responsively to the generated driving signal(s). The needle 88 is configured to vibrate in accordance with the selected vibration pattern responsively to the vibration of the actuator(s) (67-69 of FIG. 2 or 76-78 of FIG. 3) (block 206).

The pressure sensor 59 (FIG. 2) is configured to sense a level of vacuum in the aspiration channel 57 (FIG. 2) (block 208). The pressure sensor 59 provides a signal indicative of the level of vacuum to the processor 34. The processor 34 determines whether the sensed level of vacuum is below a threshold level of vacuum (decision block 210). In some embodiments, the processor 34 determines whether the sensed level of vacuum is below a threshold level of vacuum for greater than a minimum period of time at decision block 210. The sensed level of vacuum may be any suitable value, for example, in the range of 0 to 700 mmHg (millimeters of mercury). The minimum period of time may be any suitable value, for example, in the range of milliseconds to seconds.

If the sensed level of vacuum is below a threshold level of vacuum (for greater than a minimum period of time) (branch 212), the processor 34 is configured to instruct the generator 44 to alter at least one of the driving signals to transition vibration of the needle 88 (FIG. 1) from a first vibration pattern to a second vibration pattern (block 214) responsively to a decrease in the sensed level of vacuum. The processor 34 is optionally configured to start a timer (typically in software) described in more detail below. The first vibration pattern may include a longitudinal vibration pattern or a first helical vibration pattern. The second vibration pattern may include a second helical vibration pattern different from the first helical vibration pattern. In some embodiments, the processor 34 is configured to instruct the generator 44 to alter at least one of the driving signals to transition vibration of the needle 88 (FIG. 1) from the first vibration pattern to the second vibration pattern (block 214) responsively to any suitable change (e.g., increase) in the sensed level of vacuum.

If the sensed level of vacuum is not below a threshold level of vacuum (for greater than a minimum period of time) (branch 216) processing of the method returns to block 208.

In some embodiments, the amount of elliptical/circular motion versus the amount of longitudinal motion is set proportionally to the sensed vacuum so that the amount of longitudinal motion is relatively higher when the sensed vacuum is higher and the amount of elliptical/circular motion is relatively higher when the sensed vacuum is lower. For example, when the sensed vacuum is 0 mmHg the motion is 100% longitudinal and 0% elliptical/circular, when the sensed vacuum is 350 mmHg the motion is 50% longitudinal and 50% elliptical/circular, and when the sensed vacuum is 700 mmHg the motion is 0% longitudinal and 100% elliptical/circular.

Figure 7A:
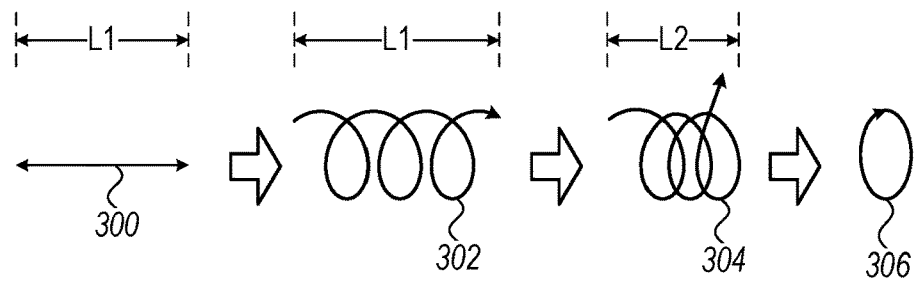
FIGS. 7A-F are schematic views illustrating different vibration pattern transitions for use in the system of FIG. 1.

Reference is now made to FIG. 7A. Reference is also made to FIG. 6. In some embodiments, the generator 44 is configured to alter at least one of the driving signals to transition vibration of the needle 88 from a longitudinal vibration pattern 300 to a helical vibration pattern 302 responsively to the decrease (or any suitable change, e.g., an increase) in the sensed level of vacuum as shown in FIG. 7A. The longitudinal vibration pattern 300 and the helical vibration pattern 302 have the same longitudinal stroke length L1 (in the Z direction, which is shown in FIG. 2). In other words, the transition from the longitudinal vibration pattern 300 to the helical vibration pattern 302 is caused by adding circular/elliptical motion to the longitudinal vibration pattern 300 without changing any longitudinal motion.

FIG. 7A also shows that the helical vibration pattern 302 transitions to another helical vibration pattern 304, which has a longitudinal stroke length of L2 which is less than the longitudinal stroke length L1. The transition from helical vibration pattern 302 to helical vibration pattern 304 is caused by reducing longitudinal motion.

In some embodiments, the generator 44 is optionally configured to alter at least one of the driving signals to further transition vibration of the needle from the helical vibration pattern 304 to a two-dimensional elliptical pattern 306 (e.g., a circular pattern) in which the tip of the needle 88 repeatedly describes a loop by moving in one direction (e.g., either clockwise or counter-clockwise) (block 218 of FIG. 6).

Figure 7B:
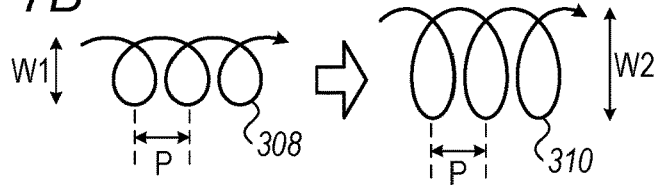

Reference is now made to FIG. 7B. In some embodiments, the generator 44 is configured to alter at least one of the driving signals to transition vibration of the needle 88 from a helical vibration pattern 308 to a helical vibration pattern 310 responsively to the decrease (or any suitable change, e.g., an increase) in the sensed level of vacuum. The helical vibration pattern 308 and the helical vibration pattern 310 have the same pitch P but different widths. The helical vibration pattern 308 has a maximum width W1. The helical vibration pattern 310 has a maximum width W2, which is greater than W1. In other words, the transition between the helical vibration pattern 308 to the helical vibration pattern 310 represents an increase in circular/elliptical motion without a change in longitudinal motion.

Figure 7C:
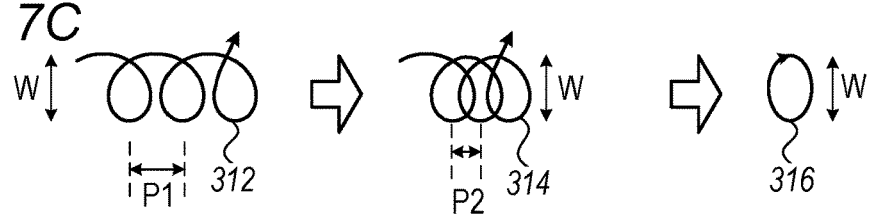

Reference is now made to FIG. 7C. In some embodiments, the generator 44 is configured to alter at least one of the driving signals to transition vibration of the needle 88 from a helical vibration pattern 312 to a helical vibration pattern 314 (and optionally to a two-dimensional elliptical vibration pattern 316 in the XY plane shown in FIG. 2) responsively to the decrease (or any suitable change, e.g., an increase) in the sensed level of vacuum. The width W of the helical vibration pattern 312 and the helical vibration pattern 314 are the same. However, the pitch P1 of the helical vibration pattern 312 is greater than the pitch P2 of the helical vibration pattern 314. The transition from the helical vibration pattern 312 to the helical vibration pattern 314 represents a reduction in longitudinal motion.

Figure 7D:
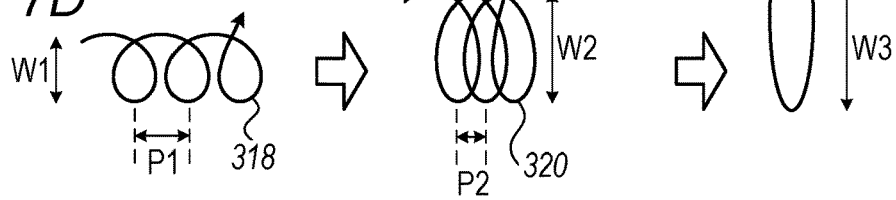

Reference is now made to FIG. 7D. In some embodiments, the generator 44 is configured to alter at least one of the driving signals to transition vibration of the needle 88 from a helical vibration pattern 318 to a helical vibration pattern 320 (and optionally to a two-dimensional elliptical vibration pattern 322 in the XY plane) responsively to the decrease (or any suitable change, e.g., an increase) in the sensed level of vacuum.

The helical vibration pattern 318 has a maximum width W1 and a pitch P1. The helical vibration pattern 320 has a maximum width W2 and a pitch P2. The two-dimensional elliptical vibration pattern 322 has a maximum width W3. The pitch P1 is greater than P2 representing a reduction in longitudinal motion. The maximum width W3 is greater than W2, which is greater than W1 representing an increase in circular or elliptical motion.

Figure 7E:
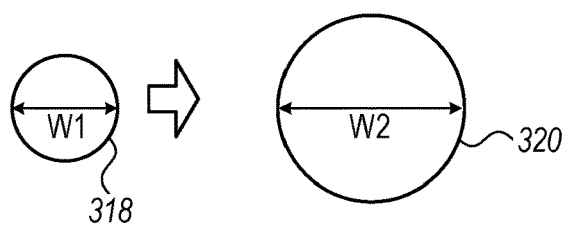

Reference is now made to FIG. 7E. In some embodiments, the helical vibration pattern 318 and helical vibration pattern 320 are circular helical patterns having a diameter equal to the maximum width W1 and W2, respectively.

Figure 7F:
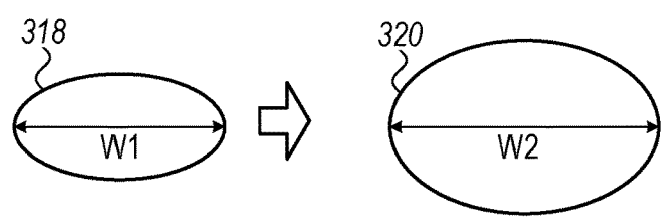

Reference is now made to FIG. 7F. In some embodiments, the helical vibration pattern 318 and helical vibration pattern 320 are elliptical helical patterns having a long axis equal to the maximum width W1 and W2, respectively.

Reference is again made to FIG. 6. The processor 34 is configured to determine if a time delay has expired from when the timer was started (or the vacuum has been restored to a sufficient level) (decision block 220). The time delay may be any suitable delay, for example, in the range of milliseconds to seconds. If the delay has expired (or the vacuum has been restored) (branch 222), the processor 34 is configured to instruct the generator 44 to alter at least one of the driving signals to further transition vibration of the needle 88 back to the first vibration pattern responsively to expiration of the delay (or responsively to restoration of the vacuum) (block 224). If the delay has not expired (or the vacuum has not been restored) (branch 226), the method returns to decision block 220.

As previously mentioned, in some embodiments, the amount of circular motion versus the amount of longitudinal motion is set proportionally to the sensed vacuum so that the amount of longitudinal motion is relatively higher when the sensed vacuum is higher and the amount of circular motion is relatively higher when the sensed vacuum is lower.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A phacoemulsification apparatus, comprising:
   a plurality of actuators configured to vibrate responsively to respective driving signals;
   a needle including an aspiration channel, and configured to be vibrated by the actuators, so as to emulsify a lens of an eye;
   a generator configured to generate at least one of the driving signals responsively to a vibration pattern selected for the needle, the needle being configured to vibrate in accordance with the selected vibration pattern; and
   a sensor configured to sense a level of vacuum in the aspiration channel, wherein the generator is configured to alter at least one of the driving signals to transition vibration of the needle from a first helical vibration pattern, to a second helical vibration pattern different from the first helical vibration pattern, responsively to a decrease in the sensed level of vacuum.

2. The apparatus according to claim 1, wherein the first helical vibration pattern includes a first pitch and the second helical vibration pattern includes a second pitch, the first pitch being greater than the second pitch.

3. The apparatus according to claim 1, wherein the first helical vibration pattern has a first maximum width and the second helical vibration pattern has a second maximum width, the second maximum width being greater than the first maximum width.

4. The apparatus according to claim 3, wherein the first helical vibration pattern includes a first pitch and the second helical vibration pattern includes a second pitch, the first pitch being greater than the second pitch.

5. The apparatus according to claim 3, wherein the first helical vibration pattern and the second helical vibration pattern are circular helical vibration patterns, the first helical vibration pattern having a diameter equal to the first maximum width, the second helical vibration pattern having a diameter equal to the second maximum width.

6. The apparatus according to claim 3, wherein the first helical vibration pattern has a long axis equal to the first maximum width, the second helical vibration pattern has a long axis equal to the second maximum width.

7. The apparatus according to claim 1, wherein the generator is configured to alter at least one of the driving signals to further transition vibration of the needle from the second helical vibration pattern to a two-dimensional elliptical pattern.

8. The apparatus according to claim 1, wherein the generator is configured to alter at least one of the driving signals to further transition vibration of the needle from the second helical vibration pattern back to the first helical vibration pattern responsively to expiration of a time delay.

9. A phacoemulsification apparatus, comprising:
   a plurality of actuators configured to vibrate responsively to respective driving signals;
   a needle including an aspiration channel, and configured to be vibrated by the actuators, so as to emulsify a lens of an eye;
   a generator configured to generate at least one of the driving signals responsively to a vibration pattern selected for the needle, the needle being configured to vibrate in accordance with the selected vibration pattern; and
   a sensor configured to sense a level of vacuum in the aspiration channel, wherein the generator is configured to alter at least one of the driving signals to transition vibration of the needle from a longitudinal vibration pattern to a helical vibration pattern, responsively to a decrease in the sensed level of vacuum, wherein the longitudinal vibration pattern has a first longitudinal stroke length, and the second helical vibration pattern has a second longitudinal stroke length, which is less than the first longitudinal stroke length.

10. A phacoemulsification method, comprising:
    generating driving signals responsively to a vibration pattern selected for vibrating a needle;
    vibrating actuators responsively to the driving signals;
    vibrating the needle in accordance with the selected vibration pattern responsively to vibrating of the actuators so as to emulsify a lens of an eye;
    sensing a level of vacuum in an aspiration channel of the needle; and
    altering at least one of the driving signals to transition vibration of the needle from a first helical vibration pattern, to a second helical vibration pattern different from the first helical vibration pattern, responsively to a decrease in the sensed level of vacuum.

11. The method according to claim 10, wherein the first helical vibration pattern includes a first pitch and the second helical vibration pattern includes a second pitch, the first pitch being greater than the second pitch.

12. The method according to claim 10, wherein the first helical vibration pattern has a first maximum width and the second helical vibration pattern has a second maximum width, the second maximum width being greater than the first maximum width.

13. The method according to claim 12, wherein the first helical vibration pattern includes a first pitch and the second helical vibration pattern includes a second pitch, the first pitch being greater than the second pitch.

14. The method according to claim 12, wherein the first helical pattern and the second helical vibration pattern are circular helical vibration patterns, the first helical vibration pattern having a diameter equal to the first maximum width, and the second helical pattern having a diameter equal to the second maximum width.

15. The method according to claim 12, wherein the first helical vibration pattern and the second helical vibration pattern are elliptical helical vibration patterns, the first helical vibration pattern having a long axis equal to the first maximum width, the second helical vibration pattern having a long axis equal to the second maximum width.

16. The method according to claim 10, further comprising altering at least one of the driving signals to further transition vibration of the needle from the second helical vibration pattern to a two-dimensional elliptical pattern responsively to a further decrease in the sensed level of vacuum.

17. The method according to claim 10, further comprising altering at least one of the driving signals to further transition vibration of the needle from the second helical vibration pattern back to the first helical vibration pattern responsively to expiration of a time delay.

* * * * *